(12) United States Patent
Kinnstaetter et al.

(10) Patent No.: US 8,090,176 B2
(45) Date of Patent: Jan. 3, 2012

(54) EVALUATION METHOD FOR A TEMPORAL SEQUENCE OF X-RAY IMAGES

(75) Inventors: Klaus Kinnstaetter, Hirschaid (DE); Thomas Redel, Poxdorf (DE)

(73) Assignee: Siemens Aktiengesellschaft, Munich (DE)

( * ) Notice: Subject to any disclaimer, the term of this patent is extended or adjusted under 35 U.S.C. 154(b) by 876 days.

(21) Appl. No.: 12/157,356

(22) Filed: Jun. 10, 2008

(65) Prior Publication Data
US 2008/0317323 A1    Dec. 25, 2008

(30) Foreign Application Priority Data

Jun. 20, 2007    (DE) .......................... 10 2007 028 226

(51) Int. Cl.
*G06K 9/00*    (2006.01)
(52) U.S. Cl. ....................................... 382/130; 382/132
(58) Field of Classification Search .................. 382/131, 382/132, 130
See application file for complete search history.

(56) References Cited

U.S. PATENT DOCUMENTS

| | | | |
|---|---|---|---|
| 5,150,292 A * | 9/1992 | Hoffmann et al. ........... | 600/431 |
| 5,297,215 A * | 3/1994 | Yamagishi ..................... | 382/131 |
| 6,496,560 B1 * | 12/2002 | Lin et al. ......................... | 378/62 |
| 6,512,807 B1 * | 1/2003 | Pohlman et al. .................. | 378/4 |
| 6,745,066 B1 * | 6/2004 | Lin et al. ....................... | 600/425 |
| 6,876,720 B2 * | 4/2005 | Tsuyuki ............................. | 378/8 |
| 7,054,406 B2 * | 5/2006 | Ikeda et al. ........................ | 378/8 |
| 7,492,947 B2 * | 2/2009 | Nanbu ........................... | 382/209 |
| 7,496,175 B2 * | 2/2009 | Sakaguchi et al. .............. | 378/95 |
| 7,715,519 B2 * | 5/2010 | Tsukagoshi et al. .............. | 378/4 |
| 7,729,525 B2 * | 6/2010 | Camus et al. .................. | 382/130 |
| 7,774,041 B2 * | 8/2010 | Nambu et al. .................. | 600/407 |
| 7,826,885 B2 * | 11/2010 | Nambu et al. .................. | 600/407 |
| 7,865,003 B2 * | 1/2011 | Camus et al. .................. | 382/128 |
| 7,912,269 B2 * | 3/2011 | Ikeda et al. .................... | 382/131 |
| 2005/0113961 A1 | 5/2005 | Sabol et al. | |
| 2007/0041625 A1 | 2/2007 | Camus et al. | |

(Continued)

FOREIGN PATENT DOCUMENTS

DE    10 2004 057 026 A1    6/2005

(Continued)

OTHER PUBLICATIONS

Thomas Wittenberg, Peter Hastreiter, Ulrich Hoppe, Heinz Handels, Alexander Horsch, Hans-Peter Meinzer; "Bildverarbeitung für die Medizin 2003"; Quantitative Analysis of Coronary-Angiographic Image Sequences for Determining Myocardial Perfusion; 2003; pp. 81-85; Image Processing for Medical Science; Springer Verlag.

(Continued)

*Primary Examiner* — Allen C. Ho (57) ABSTRACT

A computer receives a temporal sequence of x-ray images of an examination region of an examination object. The examination region includes a blood vessel system and tissue supplied with blood. A detection time is assigned in each instance to the x-ray images. The x-ray images correspond locally with one another in terms of pixels and each display a distribution of a contrast agent in the examination region at the respective detection time. The computer determines the temporal course of the temporal derivation of the data values and/or of the average value of the data values of the pixels located in the evaluation region for at least one evaluation region which is standard for all x-ray images. It assigns a type to the evaluation region as a function hereof.

14 Claims, 9 Drawing Sheets

U.S. PATENT DOCUMENTS

2007/0165920 A1     7/2007    Gering et al.

FOREIGN PATENT DOCUMENTS

DE      10 2005 039 189 A1    2/2007

OTHER PUBLICATIONS

C. Michael Gibson, Albert Schömig; "Coronary and Myocardial Angiography; Angiographic Assessment of Both Epicardial and Myocardial Perfusion", Circulation 2004, vol. 109, Issue 25; Jun. 29, 2004, pp. 3096-3105; Magazine; 2004.

Urban Malsch, Hartmut Dickhaus, Helmut Kücherer; Quantitative Analyse von koronarangiographischen Bildfolgen zur Bestimmung der Myokardperfusion, Bildverarbeitung für die Medizin 2003—Algorithmen—Systeme—Anwendungen, Springer-Verlag, pp. 81-85; Magazine; 2003.

Hrvoje Bogunovic and Sven Loncaric; "Estimating Perfusion Using X-Ray Angiography", Proceedings of the 4th International Symposium on Image and Signal Processing and Analysis (2005), pp. 147-150; Magazine; 2005.

Randall T. Higashida, Anthony J. Furlan, "Trial Design and Reporting Standards for Intra-Arterial Cerebral Thrombolysis for Acute Ischemic Stroke", Stroke 2003;34; pp. 109-137; Magazine; 2003.

Thomas A. Tomsick; "Mechanical Embolus Removal. A New Day Dawning", Stroke published online Jun. 16, 2005; Magazine; 2005.

\* cited by examiner

EVALUATION METHOD FOR A TEMPORAL SEQUENCE OF X-RAY IMAGES

CROSS REFERENCE TO RELATED APPLICATIONS

This application claims priority of German application No. 10 2007 028 226.7 filed Jun. 20, 2007, which is incorporated by reference herein in its entirety.

FIELD OF THE INVENTION

The present invention relates to an evaluation method for a temporal sequence of x-ray images of an examination region of an examination object.

BACKGROUND OF THE INVENTION

Such an evaluation method is known for instance from the technical paper "Quantitative Analyse von koronarangiographischen Bildfolgen zur Bestimmung der Myokardperfusion" [Quantitative analysis of coronary-angiographic image sequences for determining myocardial perfusion] by Urban Malsch et al., published in "Bildverarbeitung für die Medizin 2003" [Image processing for medical science 2003], Springer Verlag. With this evaluation method, a computer receives the temporal sequence of x-ray images and determines a perfusion of the tissue supplied with blood in a myocardial region.

DE 10 2005 039 189 A1 likewise discloses an evaluation method of the afore-described type. With this method, a computer also receives the temporal sequence of x-ray images. In each instance the computer determines a characteristic value for each pixel of an evaluation image for each of the x-ray images on the basis of the data values of the pixels of the respective x-ray image, which lie in an evaluation core which is standard for all x-ray images and is defined by the respective pixel of the evaluation image. On the basis of the temporal sequence of the characteristic value, it assigns the respective pixel to one of the categories comprising vessel, perfusion region and background. The computer performs further evaluations for the pixels which the computer has assigned to the perfusion region.

DE 10 2004 057 026 A1 discloses an evaluation method for several images of an examination region of an examination object which have been detected at different times. The images may be x-ray images. A computer receives the images, determines the deviations of the images from one another and performs further evaluations as a function of the "change images" thus determined.

The evaluation methods of the prior art already function pretty effectively. They can however still be further improved.

SUMMARY OF THE INVENTION

The object of the present invention consists in creating possibilities, by means of which the temporal information relating to the blood flow into the vessels can be seen more easily.

The object is achieved by an evaluation method for a temporal sequence of x-ray images of an examination region of an examination object,
  with the examination region including a blood vessel system and tissue supplied with blood by way of said blood vessel system,
  with a detection time being assigned in each instance to the x-ray images, the x-ray images corresponding locally with one another in terms of pixels and the x-ray images each displaying a distribution of a contrast agent in the examination region provided at the respective detection time,
  with a computer receiving the sequence of x-ray images, determining the temporal course of the average value of the data values of the pixels located in the evaluation region for at least one evaluation region which is standard for all x-ray images and assigning a type to the evaluation region as a function hereof.

In accordance with the invention, the computer receives the sequence of x-ray images. The computer determines the temporal course of the temporal derivation of the data values of the pixels located in the evaluation region for at least one evaluation region which is standard for all x-ray images.

Alternatively or in addition, the computer determines the temporal course of the temporal derivation of the average value of the data values of the pixels located in the evaluation region. The computer assigns a type to the evaluation region as a function of the determined temporal course and/or the determined temporal courses.

The computer program is correspondingly embodied such that the computer proceeds as above.

The core of the present invention thus consists in no longer operating with the temporal courses of the data values themselves but instead with the temporal course of the temporal derivation of the data values.

Within the scope of the evaluation, it is possible for instance for the computer to determine whether the temporal course of the temporal derivation of the average value of the data values of the pixels located in the evaluation region comprises a local maximum and a local minimum and assigns a type of a first type group and on the other hand a type of a second type group to the evaluation region in the event of the absence of the local maximum and of the local minimum.

If the local maximum and/or the local minimum are not present, the computer can
  assign a type zero to the evaluation region for instance if the absolute value of the temporal course remains below a fluctuation limit, and
  can assign a type one to the evaluation region for instance if the temporal derivation of the average value of the data values of the pixels located in the evaluation region is globally greater than zero and the maximum value of the temporal derivation of the average value of the data values of the pixels located in the evaluation region exceeds the fluctuation limit.

In the event that the local maximum and the local minimum are present, the computer can determine the position and/or width of the local maximum and of the local minimum for instance and can assign a type two or a type three to the evaluation region as a function hereof.

The types zero and one thus form the first type group. The types two and three form the second type group.

The fluctuation limit can be fixedly predetermined. Alternatively, it can be predetermined to the computer by the user (if necessary also interactively). Alternatively, it is possible for the computer to automatically determine the fluctuation limit on the basis of the sequence of x-ray images.

To decide whether the computer assigns the type two or the type three to the evaluation region, it is possible for the computer to determine the temporal sequence of the temporal derivation of the average value of the data values of the pixels located in the reference region for a reference region which is standard for all x-ray images, to determine the position and/or width of a local maximum and a local minimum of this temporal course as reference values and to decide whether to assign the type two or the type three to the evaluation region as a function of the position and/or width of the local maximum and of the local minimum of the temporal derivation of the average value of the data values of the pixels located in the evaluation region relative to the corresponding reference values.

In a particularly preferred embodiment, provision is made for the computer to assign the type two to the evaluation region if the local maximum and/or the local minimum of the temporal derivation of the average value of the data values of the pixels located in the evaluation region are temporally delayed and/or propagated relative to the corresponding reference values, and on the other hand to assign the type three.

It is possible for the evaluation region to only include one single pixel. It is alternatively possible for the evaluation region to include several pixels, for instance a block of 4×4 pixels. Other variables are however also possible.

If the evaluation region includes several pixels, it is possible for the computer, in the event that it assigns type two to the evaluation region, to determine the temporal course of the temporal derivation of the data values of these pixels for the pixels located in the evaluation region, and to evaluate these temporal courses so as to decide on the basis of this evaluation whether it retains the type two for the evaluation region or whether it assigns a type two-a or two-b to the evaluation region.

The last-mentioned procedure can be configured such that the computer determines whether the temporal courses of the temporal derivation of the data values of the pixel located in the evaluation region each comprise a local maximum and a local minimum, in the event that the local maximum and the local minimum are present in each instance, and determines the position and/or width of the respective local maximum and of the respective local minimum and assigns the type two-a to the evaluation region if the computer assigns the type two as a maximum to a first portion of the pixels located in the evaluation region and assigns a type of the first type group to the remaining pixels on the basis of a procedure in line with assigning the types of the first type group and of the type two and assigns the type two-b to the evaluation region if the computer assigns the type two to at least a second portion of the pixels located in the evaluation region on the basis of a procedure in line with assigning the type two.

The computer generally assigns a display property to a display region of an evaluation image which corresponds to the at least one evaluation region as a function of the type assigned to the evaluation region and outputs the evaluation image to a user. For instance, the evaluation image may be a color-coded display of the types assigned to the different evaluation regions.

In a preferred embodiment, provision is made for the computer to receive a closed surface as the preliminary evaluation region and to determine the evaluation region as a result such that it separates the pixels of the x-ray images which lie within the preliminary evaluation region and which correspond to the blood vessel system. This procedure is on the one hand user-friendly and enables a simple specification of the evaluation region, which on the other hand still provides for a high-quality evaluation.

BRIEF DESCRIPTION OF THE DRAWINGS

Further advantages and details result from the description below of exemplary embodiments in conjunction with the drawings, in which.

DETAILED DESCRIPTION OF THE INVENTION

Figure 1:
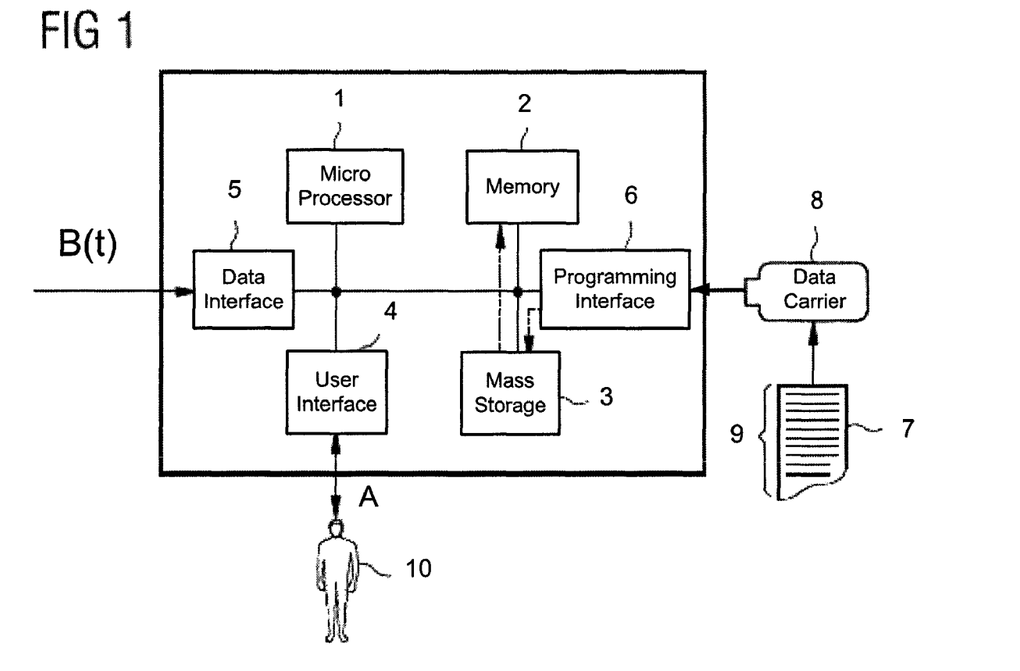
FIG. 1 shows a schematic diagram of a block diagram of an evaluation arrangement.

In accordance with FIG. 1, a computer has conventional components 1 to 6. In particular, the computer has a microprocessor 1, a working memory (RAM) 2, a mass storage device 3 (for instance a hard drive), a user interface 4, a data interface 5 and a programming interface 6. The components 1 to 6 are embodied in a conventional manner and also interact with one another in a conventional manner. The user interface 4 can include conventional input and output facilities for instance, like for example a keyboard, a mouse, a display device etc. The data interface 5 can be an internet or a LAN interface or a USB interface for instance. An embodiment as a drive for a removable storage device (for instance a CD-ROM or a DVD) is also possible. Similar embodiments are possible for the programming interface 6. If necessary, the data interface 5 and the programming interface 6 can be combined to form a common interface.

A computer program 7 is supplied to the computer by way of the programming interface 6. A data carrier 8, upon which the computer program 7 is stored in machine-readable form, is connected to the computer for instance. The computer program 7 is consequently read out from the data carrier 8 and is copied into the mass storage device 3 of the computer and is thus likewise stored there.

The computer program 7 contains machine codes 9, in other words, program instructions, which can be run directly and immediately by the computer. The computer program 7 can be called by a user 10 by means of conventional input commands (for instance a double mouse click). If the computer program 7 is called, it is loaded into the working memory 2 of the computer and run by the computer. The execution of the computer program 7 by the computer causes the computer to run a determination method, which is described in detail below in conjunction with the additional FIGS.

Figure 2:
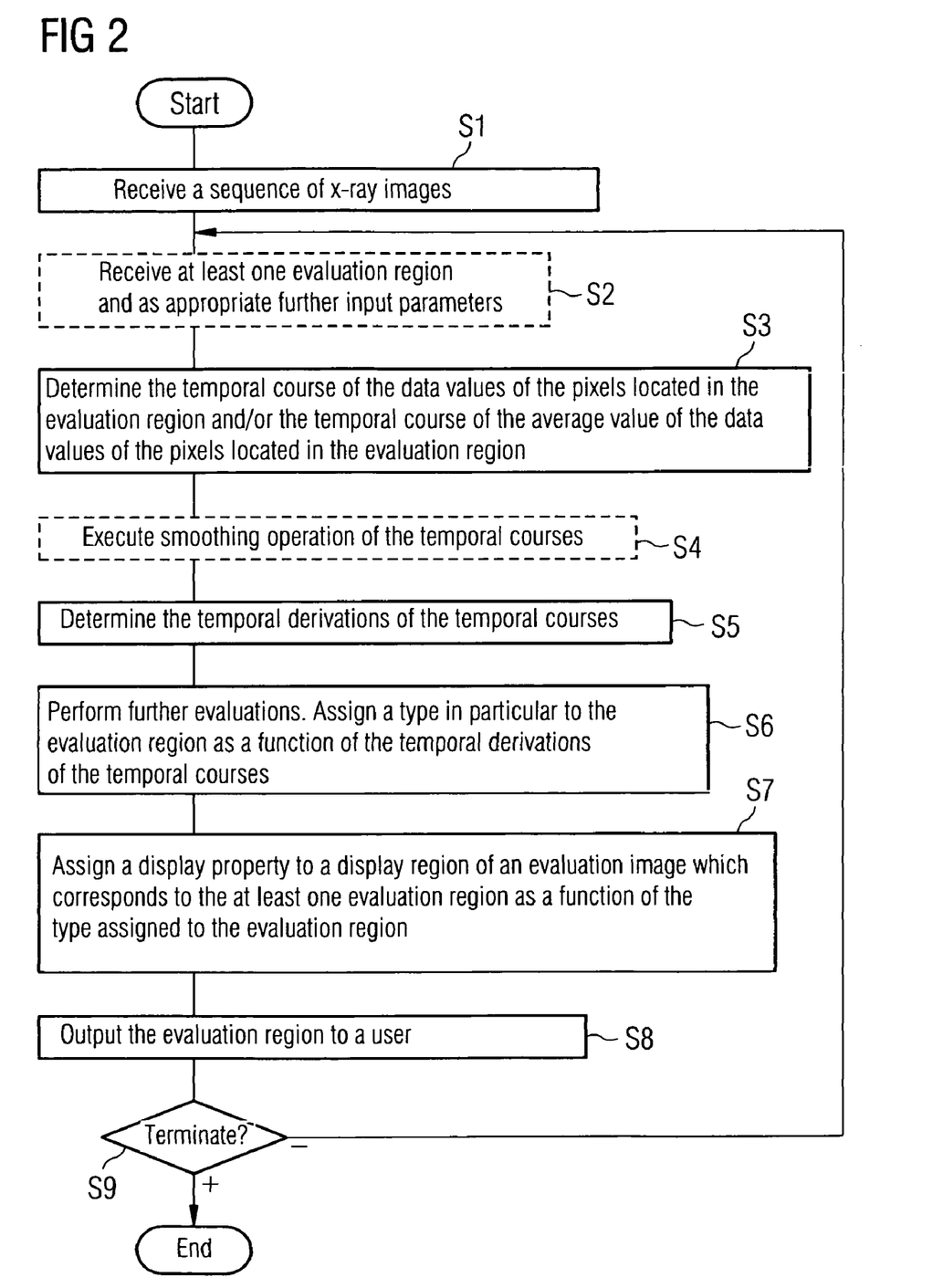
FIG. 2 shows a schematic diagram of a flow chart.

According to FIG. 2, in step S1, the computer receives a temporal sequence of x-ray images B. Based on the fact that the sequence is a temporal sequence, a detection time t is assigned to each x-ray image B, at which time the respective x-ray image B was detected. A temporal distance between two directly consecutive detection times t is in this case generally less than a second. It is in most cases even less than a quarter of a second, for instance less than a tenth of a second.

Each x-ray image B generally displays a two-dimensional distribution of a contrast agent in an examination region of an examination object provided at the respective detection time t. The contrast agent is herewith preferably injected into an artery 11 supplying the examination region (see FIG. 3). The injection is preferably carried out rapidly, in other words with a short duration and at the beginning of a high leading edge and at the end of a short trailing edge.

The examination object is generally a human. The examination region can be the brain region of the human for instance. By way of example, FIG. 3 shows an x-ray image B of an examination object.

Figure 3:
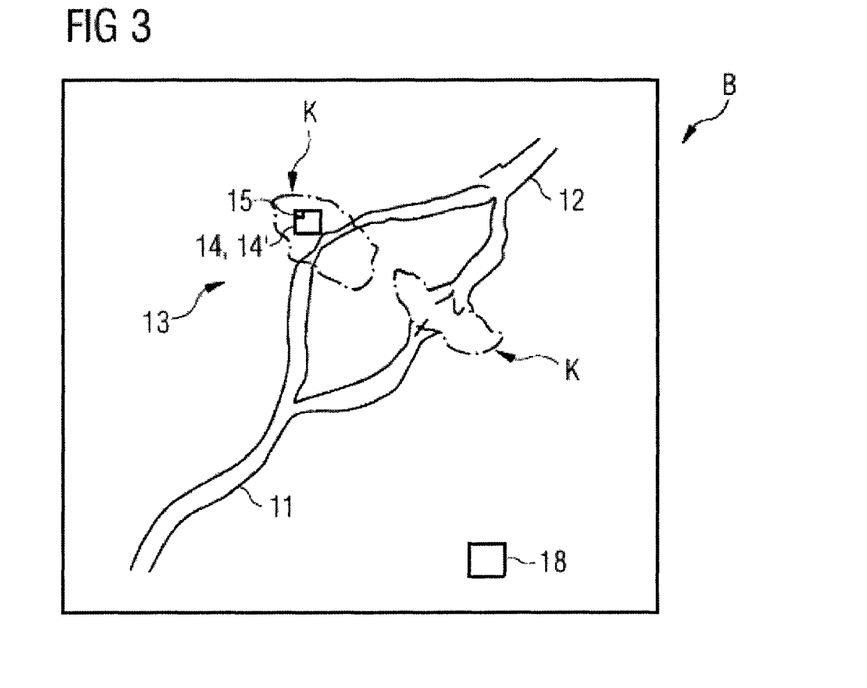
FIG. 3 shows a schematic diagram of an x-ray image.
Figure 4:
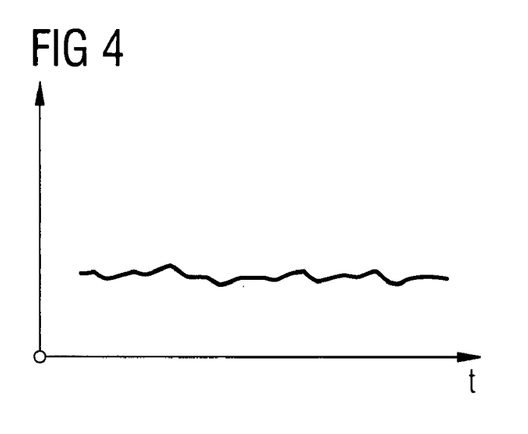
FIGS. 4 to 11 show schematic diagrams of time diagrams and FIGS. 12 to 18 show schematic diagrams of flow charts.
Figure 5:
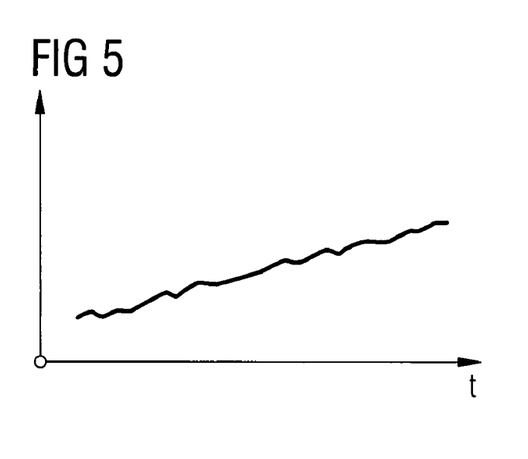
Figure 6:
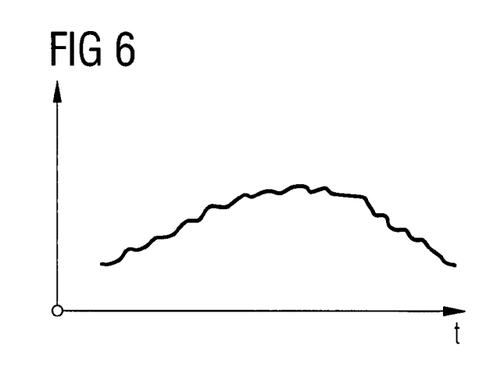
Figure 7:
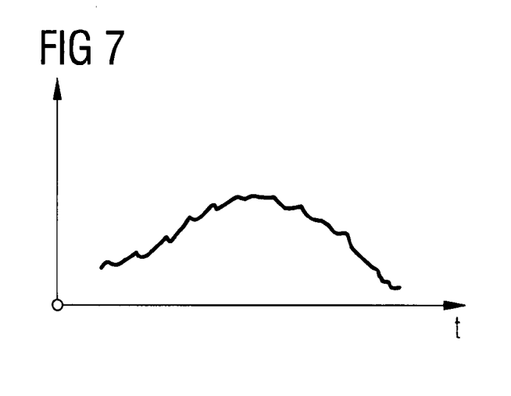
Figure 8:
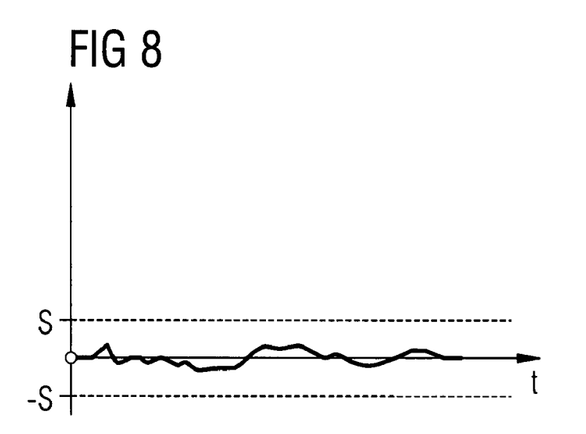
Figure 9:
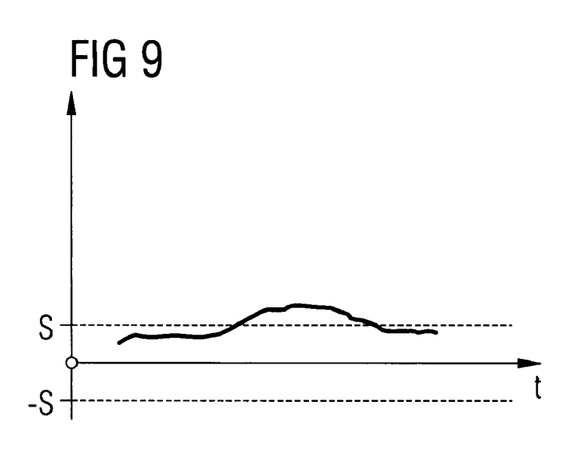

In accordance with FIG. 3, the examination region includes a blood vessel system with arteries 11 and veins 12 as well as tissue 13, with the tissue 13 being supplied with blood by way of the blood vessel system. Capillary regions K, in which the tissue anabolism between the blood and the tissue 13 takes place, thus exist between the arteries 11 of the blood vessel system and the veins 12 of the blood vessel system, see FIG. 3.

The x-ray images B are generally detected using constant imaging geometry. The x-ray images B thus correspond locally with one another in terms of pixels.

In step S2, the computer receives a selection (at least) of an evaluation region 14 (see also FIG. 3) from the user 10. The evaluation region 14 is standard for all x-ray images B. The specification of the evaluation region 14 results in the computer only executing subsequent steps within the evaluation region 14.

Step S2 is only optional and could thus be omitted. For this reason, it is only shown in FIG. 2 with a dashed line. When it is omitted, the evaluation region 14 is either fixedly predetermined or is automatically determined by the computer.

As appropriate, the computer also receives further input parameters within the scope of step S2. Reference is made again to examples of parameters of this type.

In step S3, the computer determines a temporal course of the data values of the respective pixel 15 and/or of the average value of the pixels 15 of the evaluation region 14 for each pixel 15 of the evaluation region 14 and/or for the average value of the pixels 15 of the evaluation region 14. FIGS. 4 to 7 show exemplary typically possible temporal courses of the data values.

In step S4, the computer executes a smoothing operation, for instance a low pass filtering or a fitting of a parameterizable curve. Step S4 is optional here. For this reason, it is only shown in FIG. 2 with a dashed line. It can be omitted.

In step S5, the computer determines the temporal derivation of the temporal courses determined in step S3. In the event of the absence of step S4, the computer assumes the temporal curves smoothed in step S4. By way of example, FIGS. 8 to 11 illustrate the temporal derivations of the temporal courses shown in FIGS. 4 and 7.

In step S6, the computer performs further evaluations on the basis of the temporal derivations determined in step S5. In step S7, the computer assigns a display property to a display region of an evaluation image A, which corresponds to the evaluation region 14, as a function of the type which the computer has assigned to the evaluation region 14. For instance, the computer can assign a type-specific color to the display region. In step S8, the computer outputs the evaluation image A to the user 10.

In step S9, the computer verifies whether the additional implementation of the evaluation method is to be terminated. If this is not the case, the computer returns to step S2. On the other hand, the execution of the evaluation method is terminated.

One possible embodiment of step S2 in FIG. 2 is shown in more detail below in conjunction with FIG. 12.

Figure 12:
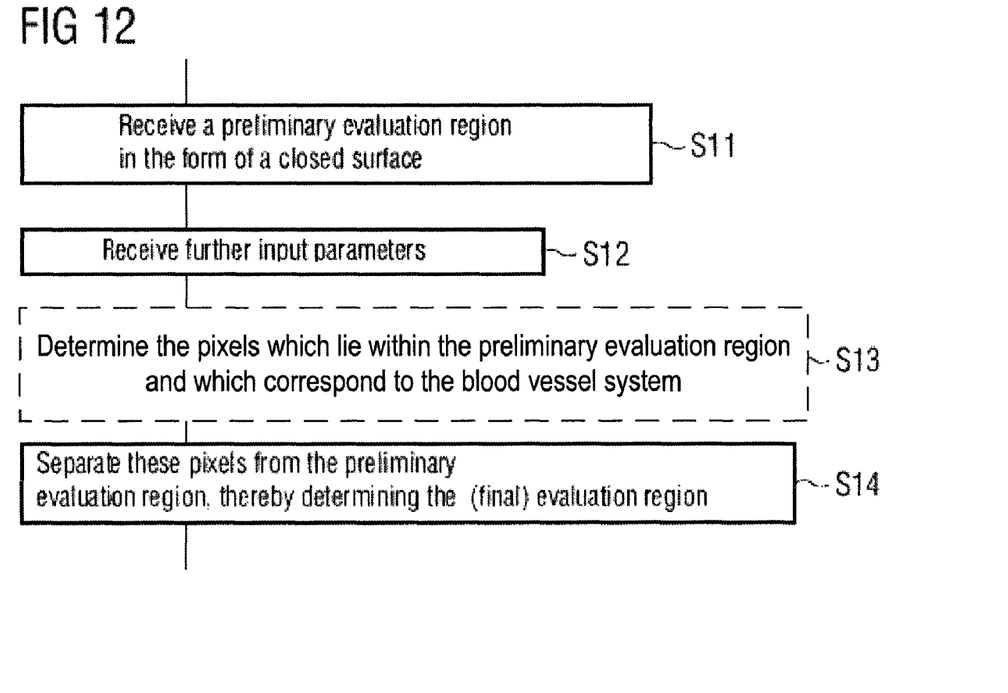

According to FIG. 12, in step S11, the computer receives the specifications of a preliminary evaluation region 14'. The preliminary evaluation region 14' corresponds here, see FIG. 3, to a closed surface. Step S11 corresponds to one part of step S2 in FIG. 2.

In step S12, the computer receives the additional input parameters.

In step S13, the computer determines those pixels 15 which lie within the preliminary evaluation region 14', and which correspond to the blood vessel system 11, 12. Step S14 allows separating the pixels determined in step S13 from the preliminary evaluation region 14'. In this embodiment, the evaluation region 14 thus only includes the pixels 15 of the preliminary evaluation region 14', which do not form an integral part of the blood vessel system 11, 12.

Step S13 in FIG. 12 is only optional and is only shown with a dashed line in FIG. 12 for this reason. If it is omitted, within the scope of the embodiment in FIG. 12, the corresponding pixels 15 must be made known to the computer in another manner.

Different procedures are possible in order to realize the evaluation of the temporal derivations. Preferred evaluation methods which are based on one another are described in more detail below in conjunction with FIGS. 13 to 17.

Figure 13:
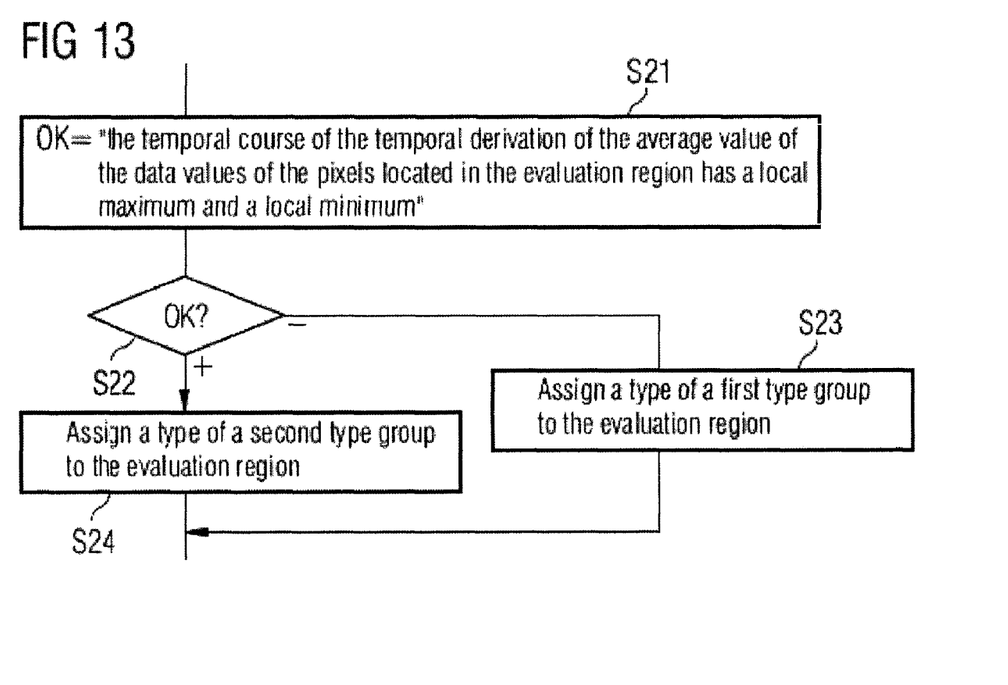

According to FIG. 13, in step S21, the computer firstly determines a logical variable OK. The logical variable OK then assumes the value "TRUE" and only then if the temporal course of the temporal derivation of the average value of the data values of the pixels 15 located in the evaluation region 14 has both a local maximum 16 and also a local minimum 17. The term "local maximum" is to mean here that the temporal derivation has lower values prior to and after the maximum value of the temporal derivation. The term "local minimum" is to be understood in a similar fashion.

In step S22, the computer verifies the value of the logical variable OK. Depending on the result of the verification of step S22, the computer subsequently performs a step S23 or a step S24.

In step S23, the computer assigns a type of a first type group to the evaluation region 14. In step S24, the computer assigns a type of a second type group to the evaluation region 14. For instance, the computer can assign a type of the first type group to temporal derivations according to FIGS. 8 and 9, and a type of the second type group to temporal derivations according to FIGS. 10 and 11.

Figure 14:
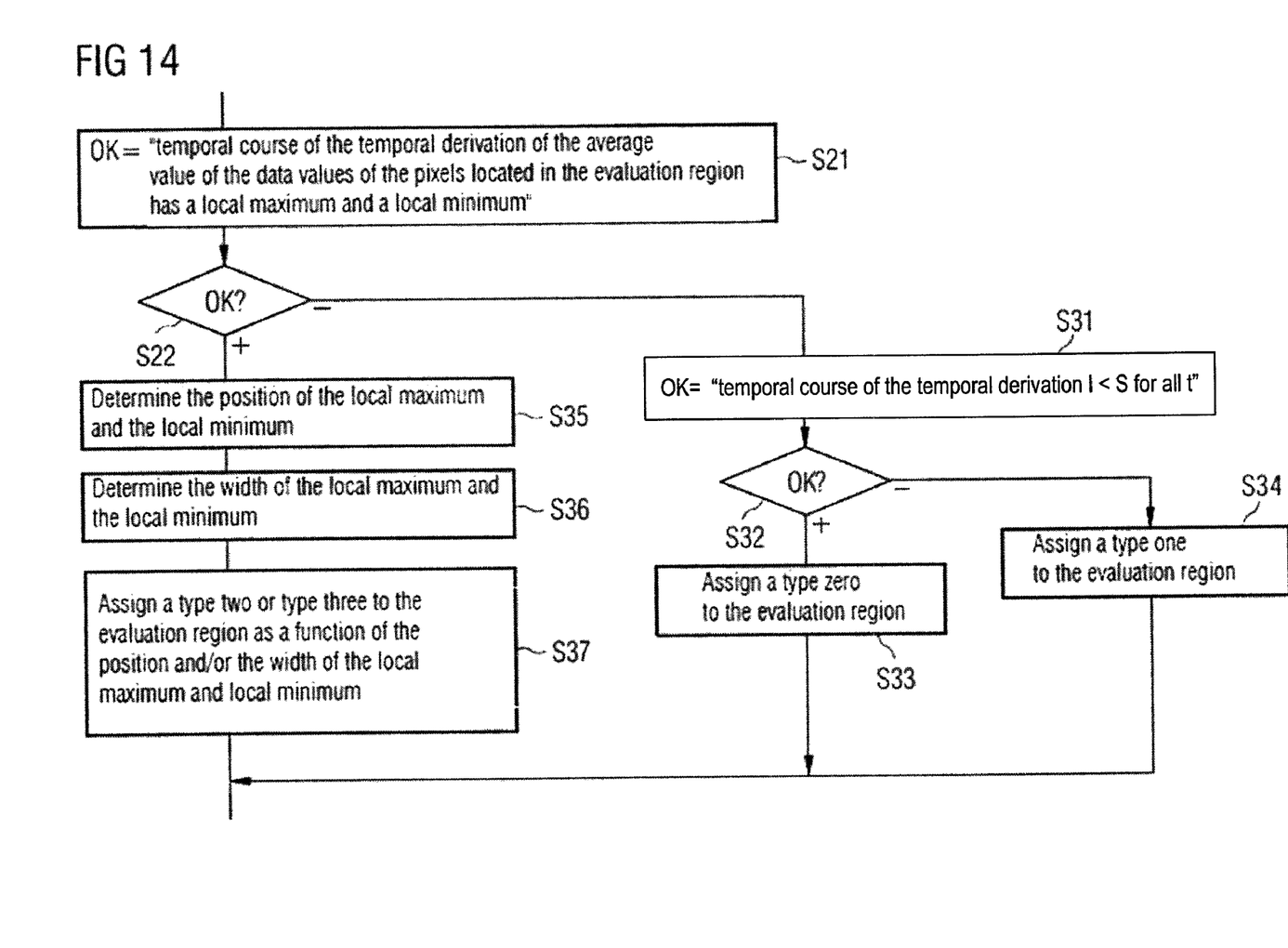

According FIG. 14, in other words in the event that the local maximum 16 and/or the local minimum 17 are not present on the one hand and that the local maximum 16 and the local minimum 17 (both) are present on the other hand, the steps S23 and S24 in FIG. 14 are embodied as follows:

In step S31, the computer redetermines the value of the logical variable OK. The logical variable OK then in this case assumes the value "TRUE" and only then if the absolute value of the temporal course remains below a fluctuation limit S (see FIG. 8).

In step S32, the computer verifies the value of the logical variable OK. If the logical variable OK has the value "TRUE", the computer executes a step S33, in which it assigns a type zero to the evaluation region 14. If the logical variable OK has the value "FALSE", the absolute value of the temporal course is forced to exceed the fluctuation limit S (see FIG. 9) at least once (in other words locally). For systematic reasons, the temporal derivation is in this case also globally (in other words for all values) larger than zero. In this case, the computer assigns a type one to the evaluation region 14 in step S34.

Figure 10:
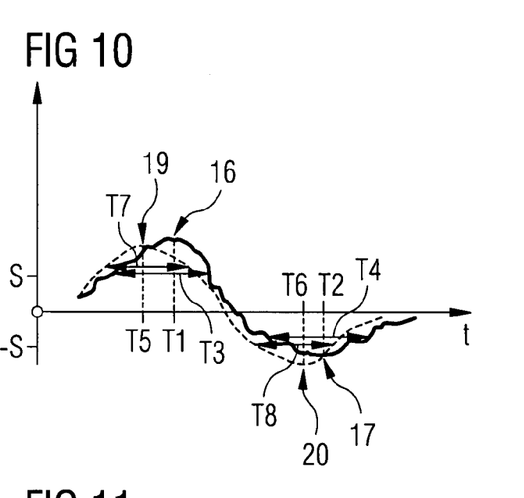
Figure 11:
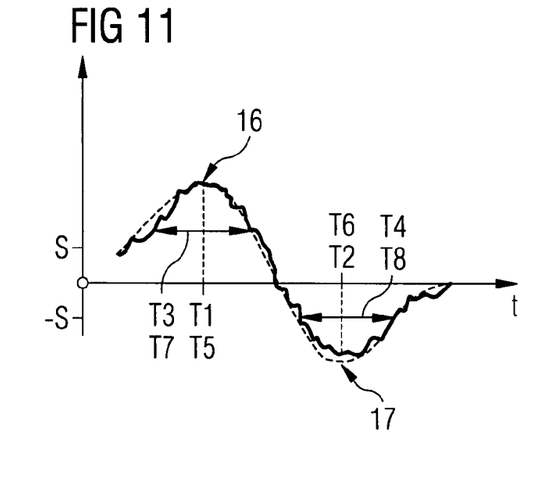

In step S35, the computer can also determine the position T1 of the local maximum 16 and the position T2 of the local minimum 17 (see FIGS. 10 and 11). Alternatively or in addition, in step S36, the computer can determine the width T3 of the local maximum 16 and the width T4 of the local minimum 17. In step S37, the computer can then assign a type two or a type three to the evaluation region 14 as a function of the position T1, T2 and/or the width T3, T4 of the local maximum 16 and of the local minimum 17.

Step S37 in FIG. 14 can be embodied in accordance with FIG. 15 as follows for instance.

Figure 15:
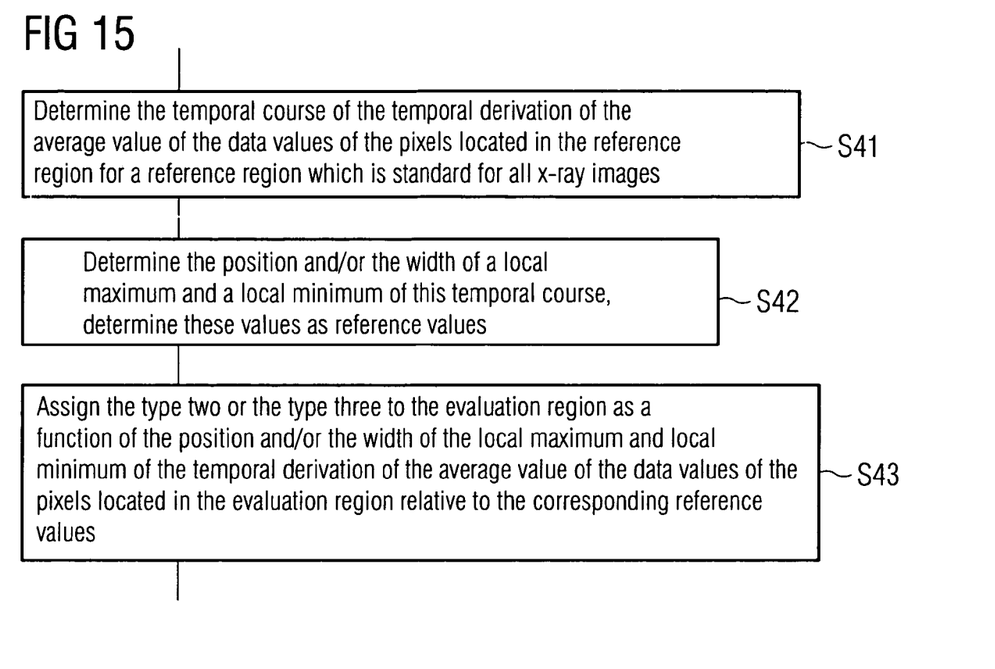

According to FIG. 15, in step S41, the computer determines the temporal course of the temporal derivation of the average value of the data values of pixels which are located in the reference region 18 for a reference region 18. The step S41 corresponds to steps S3 and S5 in FIG. 2 in respect of its basic procedure. Here the reference region 18 can be predetermined to the computer by the user 10.

In step S42, the computer determines the positions T5, T6 of a local maximum 19 and a local minimum 20. The local maximum 19 and the local minimum 20 are related here to the temporal derivation of the course, which was determined on the basis of the reference region 18. Similarly, the computer determines widths T7, T8 of this local maximum 19 and this local minimum 20 within the scope of step S42. The values T5 and T8 thus determined form reference values T5 to T8. Step S42 corresponds to steps S35 and S36 in FIG. 14 in respect of its procedure.

In step S43, the computer alternatively assigns the type two or the type three to the evaluation region 14. The computer decides here whether to assign the type two or the type three to the evaluation region 14, as a function of the position T1, T2 and/or the width T3, T4 of the local maximum 16 and the local minimum 17 of the temporal derivation of the data values of the pixels 15 located in the evaluation region 14 relative to the corresponding reference values T5 and T8.

Figure 16:
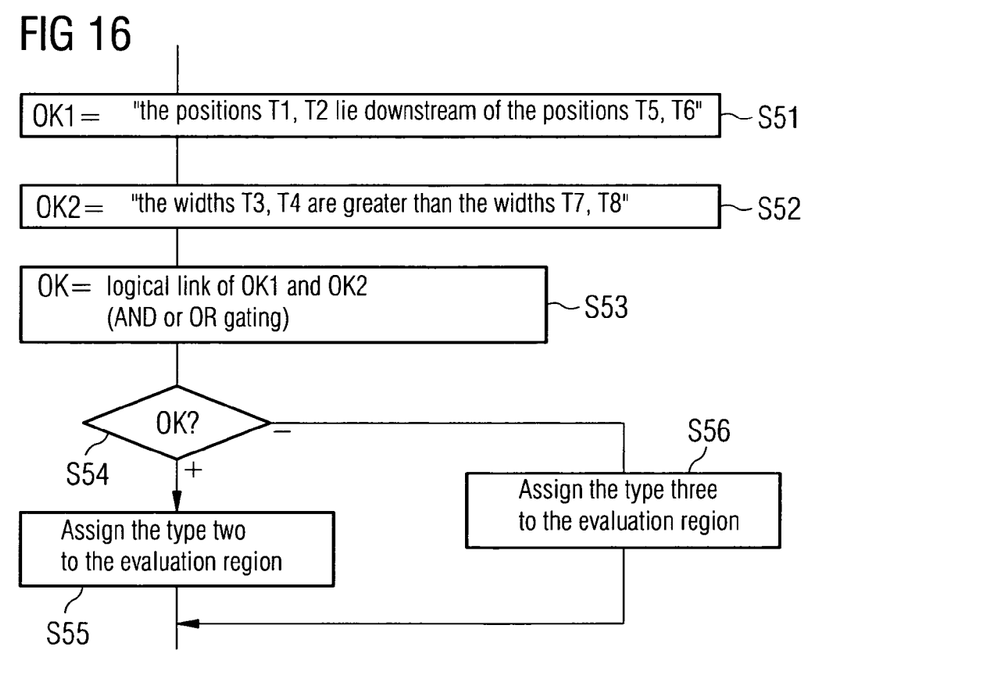

Step S43 can be embodied in accordance with FIG. 16 as follows for instance:

In steps S51 and S52, the computer determines logical variables OK1 and OK2. The logical variable OK1 then assumes the value "TRUE" here and only then if the positions T1, T2 lie downstream of the positions T5, T6 to a noticeable extent, for instance more than 5% to 10%. The logical variable OK2 then assumes the value "TRUE" and only then if the widths T3, T4 are greater than the widths T7, T8 to a noticeable extent—by more than 5% to 10% for instance.

One of steps S51 and S53 can be omitted. If both steps are present, the computer determines the logical variable OK by means of a logical link (alternatively AND gating or OR gating) of the logical variables OK1 and OK2 in step S53.

In step S54, the computer verifies the value of the logical variables OK. Depending on the result of the verification, the computer executes a step S55 or a step S56 as the next step. In step S55, the computer assigns the type two to the evaluation region 14 and the type three in step S56.

The previously described procedures can be realized irrespective of the size of the evaluation region 14. In particular, they can be realized irrespective of whether the evaluation region 14 has only one single pixel 15 or whether the evaluation region 14 has several pixels 15. In the event that the evaluation region 14 has several pixels 15, it is possible (however not imperative) to subsequently assign step S55 with steps S61 and S63, which are described in more detail below in conjunction with FIG. 17.

Figure 17:
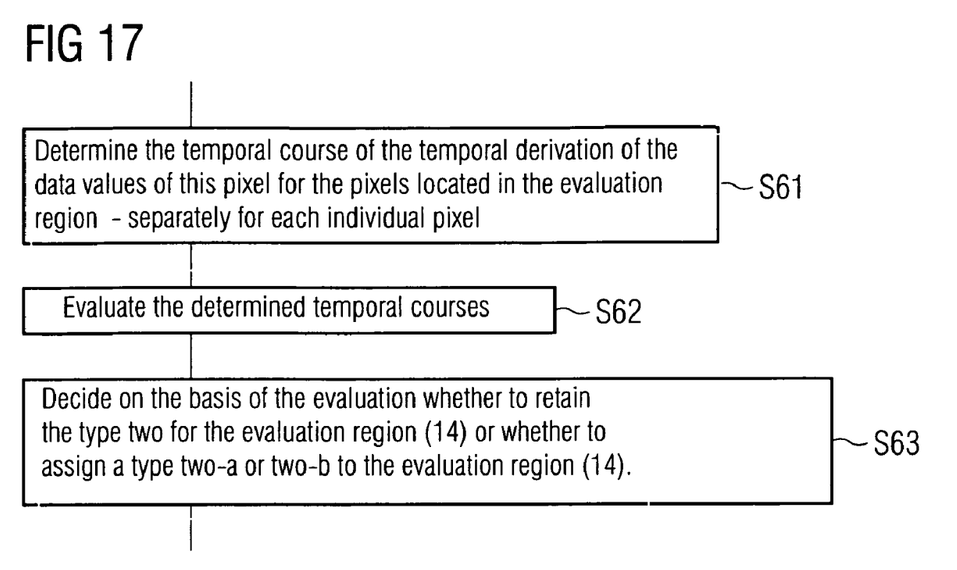

According to FIG. 17, in step S61, the computer can determine the temporal course of the temporal derivation of the data values of these pixels 15 for the pixels 15 located in the evaluation region 14. Step S61 is implemented here separately for each individual pixel 15.

In step S62, the computer evaluates the temporal courses determined in step S61. In step S63, the computer decides on the basis of this evaluation whether or not to retain the type two for the evaluation region 14. If the computer does not retain the type two, it assigns either type two-a or type two-b to the evaluation region 14. Within the scope of this embodiment, a detailed account is shown of how this is explained below in conjunction with FIG. 18.

Figure 18:
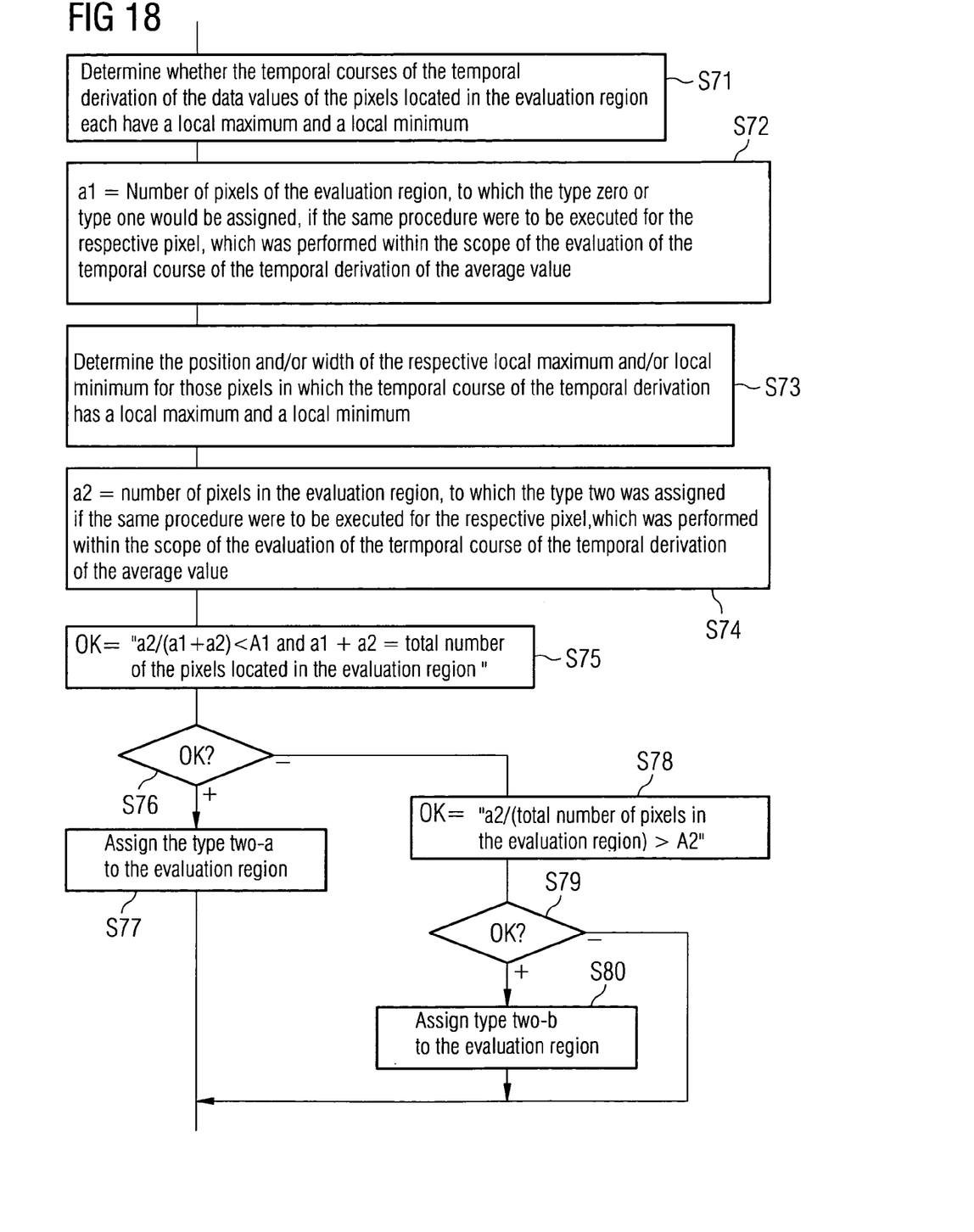

According to FIG. 18, in step S71 the computer determines whether the temporal courses of the temporal derivation of the data values of the pixels 15 located in the evaluation region 14 has a local maximum and a local minimum in each instance. Step S71 corresponds in its approach to step S21 in FIG. 13. The difference is that it is implemented individually for each pixel 15.

In step S72, the computer determines a first portion a1. The portion a1 corresponds to the number of pixels 15 of the evaluation region 14, to which the computer would assign the type zero or the type one, if it were to execute the same procedure for the respective pixel 15 which was performed within the scope of the evaluation of the temporal course of the temporal derivation of the average value.

For those pixels 15, in which the temporal course of the temporal derivation has a local maximum and a local minimum, in step S73, the computer determines the positions and/or the widths of the respective local maximum and/or local minimum. Step S73 corresponds in its approach to steps S35 and S36 in FIG. 14.

In step S74, the computer determines a portion a2. The portion a2 corresponds to the number of pixels 15 of the evaluation region 14, to which the computer would assign the type two, if it were to adopt the same procedure which it adopted in respect of the temporal course of the temporal derivation of the average value of the data values for the temporal courses of the temporal derivations of the data values of the individual pixels 15.

In step S75, the computer determines the value of the logical variable OK. In this case, the logical variable OK then receives the value "TRUE" and only then if the number a2, divided by the sum of the numbers a1 and a2, lies below a first portion A1 and the sum of the numbers a1 and a2 corresponds to the total number of the pixels 15 located in the evaluation region 14. In step S76, the computer verifies the value of the logical variable OK. If the logical variable OK in this case has the value "TRUE", the computer assigns the type two-a to the evaluation region 14 in step S77. The portion A1 can lie between 60 and 70% for instance, in particular at approximately ⅔.

In step S78, the computer likewise determines the value of the logical variable OK. In this case, logical variable OK then assumes the value "TRUE" and only then if the number a2, in respect of the total number of pixels 15 located in the evaluation region 14, exceeds a second portion A2. In step S79, the computer verifies the value of the logical variable OK. In this case, the computer assigns the type two-b to the evaluation region 14 in step S80. The second portion A2 is considerably larger here than the first portion A1. It generally lies above 90%, in particular above 95%. It can even reach 100%.

If the computer assigns either the type two-a or the type two-b to the evaluation region 14, it retains type two for the evaluation region 14.

The teaching of the present invention was described above in conjunction with a single evaluation region 14. It is however naturally possible to specify several evaluation regions 14 to the computer simultaneously and to implement the afore-described procedures independently of one another for each of the evaluation regions 14. By way of example, the computer can subdivide the x-ray images B into a number of equally sized lots, with each lot corresponding to its own, if necessary preliminary, evaluation region 14, 14'.

The present invention has many advantages. In particular, a considerably more precise evaluation than in the prior art is possible in a simple fashion.

The above description is used exclusively to explain the present invention. By contrast, the scope of protection of the present invention is to be determined exclusively by means of the appended claims.

The invention claimed is:

1. A method for evaluating a temporal sequence of x-ray images of an examination region of an examination object, the method comprising:
processing in a processor the sequence of x-ray images, said processing comprising:
assigning a sequence of detection times each corresponding to each of the x-ray images;
defining an evaluation region in the examination region;
determining a temporal course of a temporal derivation of an average value of pixels of x-ray images located in the evaluation region based on the corresponding detection times; and
assigning a type to the evaluation region based on the temporal course, wherein at least a first type group is assigned to the evaluation region if the temporal course has a local maximum and a local minimum, and further wherein at least a second type group is assigned to the evaluation region if the temporal course lacks the local maximum and the local minimum.

2. The method as claimed in claim 1, wherein the examination region comprises a blood vessel system and tissue supplied with blood by the blood vessel system.

3. The method as claimed in claim 2,
wherein a closed surface is defined as a preliminary evaluation region, and
wherein the evaluation region is defined for separating pixels of x-ray images in the preliminary evaluation region and pixels of x-ray images in the blood vessel system.

4. The method as claimed in claim 1, wherein the sequence of x-ray images displays a sequence of distributions of a contrast agent in the examination region at the corresponding detection times.

5. The method as claimed in claim 1, wherein the evaluation region is standard for all the x-ray images.

6. The method as claimed in claim 1,
wherein a type zero is assigned to the second type group of the evaluation region if an absolute value of the temporal course remains below a fluctuation limit, and
wherein a type one is assigned to the second type group of the evaluation region if the temporal derivation is greater than zero and a maximum value of the temporal derivation exceeds the fluctuation limit.

7. The method as claimed in claim 6,
wherein positions or widths of the local maximum and the local minimum are determined, and
wherein a type two or a type three is assigned to the evaluation region as a function of the determination.

8. The method as claimed in claim 7,
wherein a reference temporal course of temporal derivation of an average value of pixels located in a reference region which is standard for all the x-ray images is determined,
wherein positions or widths of a local maximum and a local minimum of the reference temporal course are determined as reference values, and
wherein the type two or the type three is assigned to the evaluation region as a function of the positions or the widths of the local maximum and the local minimum of the temporal derivation in the evaluation region relative to the corresponding reference values.

9. The method as claimed in claim 8,
wherein the type two is assigned to the evaluation region if the local maximum or the local minimum of the temporal in the evaluation region is temporally delayed or propagated relative to the corresponding reference values, and
wherein the type three is assigned to the evaluation region if the local maximum or the local minimum of the temporal in the evaluation region is not temporally delayed or propagated relative to the corresponding reference values.

10. The method as claimed in claim 9,
wherein temporal courses of temporal derivations of pixels of x-ray images located in the evaluation region are determined for each of the pixels,
wherein the temporal courses are evaluated, and
wherein a decision of whether to retain the type two to the evaluation region or whether to assign a type two-a or two-b to the evaluation region is made based on the evaluation.

11. The method as claimed in claim 10,
wherein positions or widths of local maximums and local minimums for the temporal courses are determined if the temporal courses have the local maximums and the local minimums,
wherein the type two-a is assigned to the evaluation region if the type two is assigned as a maximum to a first portion of the pixels and the first type group is assigned to remaining pixels, and
wherein the type two-b is assigned to the evaluation region if the type two is assigned to a second portion of the pixels.

12. The method as claimed in claim 1, further comprising assigning a display property to a display region of the x-ray images located in the evaluation region as a function of the type assigned to the evaluation region.

13. A data carrier executed on a computer for evaluating a temporal sequence of x-ray images of an examination region of an examination object, comprising:
a computer program stored in a non-transitory tangible computer-readable medium, said program when executed by the computer configured to:
assign a sequence of detection times each corresponding to each of the x-ray images,
define an evaluation region in the examination region,
determine a temporal course of a temporal derivation of an average value of pixels of x-ray images located in the evaluation region based on the corresponding detection times, and
assign a type to the evaluation region based on the temporal course, wherein at least a first type group is assigned to the evaluation region if the temporal course has a local maximum and a local minimum, and further wherein at least a second type group is assigned to the evaluation region if the temporal course lacks the local maximum and the local minimum.

14. Apparatus for evaluating a temporal sequence of x-ray images of an examination region of an examination object, comprising:
an image recording device configured to record the temporal sequence of the x-ray images; and
a processor configured to:
assign a sequence of detection times each corresponding to each of the x-ray images,
define an evaluation region in the examination region,
determine a temporal course of a temporal derivation of an average value of pixels of x-ray images located in the evaluation region based on the corresponding detection times, and assign a type to the evaluation region based on the temporal course, wherein at least a first type group is assigned to the evaluation region if the temporal course has a local maximum and a local minimum, and further wherein at least a second type group is assigned to the evaluation region if the temporal course lacks the local maximum and the local minimum.

* * * * *